United States Patent [19]

Corriu et al.

[11] Patent Number: 4,617,413
[45] Date of Patent: Oct. 14, 1986

[54] PENTACOORDINATE SILICON COMPLEXES, THE PROCESS FOR THEIR PREPARATION AND THEIR APPLICATION TO THE PREPARATION OF ORGANOSILANES

[75] Inventors: Robert J. Corriu; Geneviève E. Cerveau, both of Montpellier; Claude G. Chuit, Palavas les Flots; Catherine Reye, Montpellier, all of France

[73] Assignee: Centre National de la Recherche Scientifique, Paris, France

[21] Appl. No.: 813,740

[22] Filed: Dec. 24, 1985

[30] Foreign Application Priority Data

Dec. 27, 1984 [FR] France ................ 84 19885

[51] Int. Cl.$^4$ .................... C07F 7/08; C07F 7/18
[52] U.S. Cl. .................... 556/464; 556/406; 556/463; 556/466; 556/478; 556/487; 556/489
[58] Field of Search ............ 556/464, 466, 478, 489, 556/487, 406, 463

[56] References Cited

U.S. PATENT DOCUMENTS

| | | | |
|---|---|---|---|
| 3,360,525 | 12/1967 | Frye | 556/464 X |
| 3,455,980 | 7/1969 | Frye | 556/464 X |
| 3,555,069 | 1/1971 | Frye | 556/464 X |
| 4,447,628 | 5/1984 | Farnham | 556/464 X |
| 4,528,389 | 7/1985 | Farnham | 556/464 X |

Primary Examiner—Paul F. Shaver
Attorney, Agent, or Firm—Fulbright & Jaworski

[57] ABSTRACT

The present invention relates to new pentacoordinate silicon complexes, the process for their preparation and their application to the preparation of organosilanes.

The pentacoordinate silicon complexes according to the invention correspond to the general formula I:

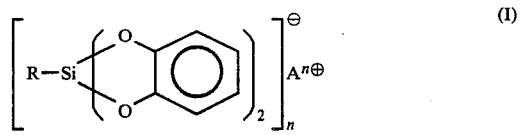

in which:
R denotes an alkyl, alkenyl, alkynyl, aryl, aralkyl, aralkenyl, aralkynyl or alkylaryl radical in which the aliphatic fragments are linear, branched or cyclic and contain from 1 to 20 carbon atoms,
A represents an alkali metal or alkaline earth metal, with the proviso however that A represents neither sodium nor potassium when R is a phenyl radical, and
$n=1$ or 2.

13 Claims, No Drawings

PENTACOORDINATE SILICON COMPLEXES, THE PROCESS FOR THEIR PREPARATION AND THEIR APPLICATION TO THE PREPARATION OF ORGANOSILANES

The present invention relates to new pentacoordinate silicon complexes and the process for their preparation.

The pentacoordinate silicon complexes according to the invention correspond to the general formula I:

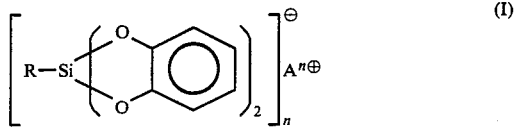

in which:
R denotes an alkyl, alkenyl, alkynyl, aryl, aralkyl, aralkenyl, aralkynyl or alkylaryl radical in which the aliphatic fragments are linear, branched or cyclic and contain from 1 to 20 carbon atoms,
A represents an alkali metal or alkaline earth metal, with the proviso however that A represents neither sodium nor potassium when R is a phenyl radical, and
n=1 or 2.

Throughout the present description, the aryl radicals and the aromatic fragments of the aralkyl, aralkenyl, aralkynyl and alkylaryl radicals denote phenyl and naphthyl radicals.

According to the present invention, these complexes of the general formula I are obtained by reacting a silicon derivative of the general formula II:

R—SiY (II)

in which:
R has the meaning given in claim 1 and
Y represents a $C_1$ to $C_6$ trialkoxy, trihalogeno, $C_1$ to $C_6$ dialkoxyhydrogeno or dihalogenohydrogeno group, with pyrocatechol in the presence of a base.

The starting materials of the general formula II can be prepared by conventional process described, for example, in "Chemistry and Technology of Silicones" (W. Noll).

An alkali metal alcoholate or alkaline earth metal alcoholate, for example sodium methylate, may advantageously be used as the base necessary for carrying out the above process, it being possible in particular for the said alcoholate to be prepared in situ in the reaction medium.

In general, the reaction of the silicon derivative of the formula (II), R—SiY, with pyrocatechol is carried out in an anhydrous solvent medium, especially an alcoholic medium such as methanol, and under an inert atmosphere, in particular a nitrogen atmosphere.

The present invention also relates to the application of the complexes of the formula I to the preparation of organosilanes, these compounds being capable of numerous industrial applications.

Organosilanes are usually prepared by heating elemental silicon with an alkyl or aryl halide in the presence of a copper-based catalyst. This type of reaction has the disadvantage that it most frequently leads to mixtures of various products. Thus, the reaction of silicon with methyl chloride produces a mixture of methylchlorosilanes according to the following reaction scheme:

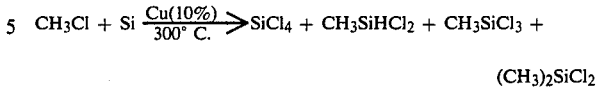

$(CH_3)_2SiCl_2$

Moreover, mixed organosilanes containing different organic groups cannot be obtained directly by this type of preparative method.

The closest known state of the art can be illustrated by U.S. Pat. No. 3,360,525, which relates to a very general family of pentacoordinate silicon complexes of which only sodium bis(benzene-1,2-diolato)phenylsilicate is described. However, these complexes are presented as having a different application since they are said to be usable directly as catalysts or vulcanizing agents for various molding materials such as epoxy resins and silicone rubbers.

According to the present invention, all the complexes of the general formula I are used without restriction as starting materials for the preparation of organosilanes of the formula III:

RR'R"SiR''' (III)

in which:
R has the meaning given above,
R' denotes a radical R and
R" and R''' denote a hydrogen atom or a radical R, it also being possible for R' and R" to form a ring with the silicon atom.

These organosilanes of the formula III are prepared by reacting the said complexes of the formula I, without any restriction, with organometallic derivatives.

The majority of the organosilanes of the formula III obtained according to the invention are known. They are essentially used in the silicone industry as cross-linking agents and additives for catalyst compositions, or alternatively in the pharmaceutical industry. They have been prepared hitherto from starting materials resulting from the direct synthesis referred to above, by processes requiring a large number of reaction steps.

By contrast, the present invention offers a new route for the synthesis of organosilanes which requires no more than two reaction steps and which enables very pure products to be obtained with excellent yields. This method of preparation also makes it possible rapidly to obtain a very wide variety of mixed organosilanes.

The organometallic derivatives used for this purpose are compounds having at least one organic group joined to a metal atom by a direct carbon-metal bond.

The organic groups present in the organo-metallic derivatives principally consist of hydrocarbon radicals chosen from the group comprising alkyl, alkenyl, alkynyl, aryl, aralkyl, aralkenyl, aralkynyl or alkylaryl radicals in which the aliphatic fragments are linear, branched or cyclic and contain from 1 to 20 carbon atoms.

Principal examples which may be mentioned of the metals present in such organometallic derivatives are the alkali metals, the alkaline earth metals, the metals of group III, such as aluminum, and the transition metals, such as zinc.

Particular examples which may be mentioned are the alkali metal organometallic derivatives of the general formula IV:

R—Alk  (IV)

in which R has the meaning given above and Alk denotes an alkali metal, such as methylsodium and methyllithium, ethylsodium and ethyllithium, isopropylsodium and isopropyllithium, n-butylsodium and n-butyllithium, vinylsodium and vinyllithium, allylsodium and allyllithium, ethynylsodium and ethynyllithium, propargylsodium and propargyllithium, phenylsodium and phenyllithium and benzylsodium and benzyllithium; the organomagnesium halides of the general formula V:

R—Mg—X  (V)

in which R has the meaning given above and X denotes a halogen atom, such as methylmagnesium bromide, ethylmagnesium bromide, isopropylmagnesium bromide, tert.butylmagnesium bromide, vinylmagnesium bromide, allylmagnesium bromide, hexynylmagnesium bromide, phenylmagnesium bromide, benzylmagnesium bromide and phenylethynylmagnesium bromide; the organozinc derivatives of the general formula VI:

R₂Zn  (VI)

in which R has the meaning given above, such as diethylzinc; the organodimagnesium derivatives of the general formula VII:

  (VII)

in which Z denotes an alkylene or alkenylene radical containing 3 to 5 carbon atoms and X denotes a halogen atom, such as pentyl-1,5-dimagnesium dichloride, pentyl-1,5-dimagnesium dibromide and but-2(Z)-enyl-1,4-dimagnesium dichloride; and the di(alkyl metal) organometallic derivatives of the general formula VIII:

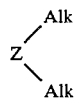  (VIII)

in which Z denotes an optionally substituted alkylene or alkenylene radical containing 3 to 5 carbon atoms and Alk denotes an alkali metal or alkaline earth metal, such as:

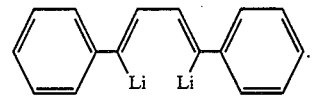

According to another characteristic of the present invention, the reaction of the organometallic derivative with the pentacoordinate silicon complex of the general formula I is carried out by heating under reflux in an anhydrous solvent medium and under an inert atmosphere, for example under a nitrogen atmosphere. The inert solvent medium used is advantageously chosen from aliphatic ethers, such as ethyl ether, dioxane and tetrahydrofuran, or alternatively from hydrocarbons, such as, for example, cyclohexane.

In one variant, after the reaction of the organometallic derivative with the complex of the formula I has been carried out, a reducing agent, in particular an inorganic hydride such as lithium aluminum hydride, can be introduced to give a monohydrogenoorganosilane of the formula III in which R''' represents a hydrogen atom.

Finally, the said reaction of the organometallic derivative with the complex of the formula I can be carried out in the presence of bis(cyclopentadienyl)-titanium dichloride to give either a monohydrogenoorganosilane derivative or a dihydrogenoorganosilane derivative in the case where the radical R of the organometallic derivative is hindered. The dihydrogenoorganosilane thus obtained can in turn be reacted with a second organometallic derivative, for example an alkylmagnesium halide, to give a monohydrogenosilane.

A number of examples of the preparation of silicon complexes and organosilanes obtained according to various modified versions are now given below in order to illustrate the invention.

EXAMPLE 1

Preparation of sodium bis(benzene-1,2-diolato)methylsilicate

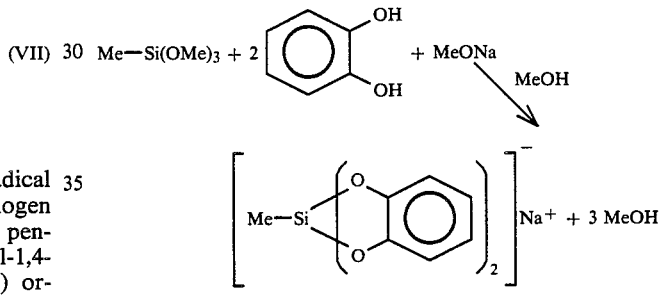

The preparation is carried out under nitrogen in a Schlenk tube with degassed solvents.

1.09 g of sodium (0.0475 mol) are dissolved in 15 ml of methanol. 6.47 g of MeSi(OMe)₃ (0.0475 mol) diluted in 10 ml of methanol are added rapidly at room temperature. A solution of 10.34 g of pyrocatechol in 20 ml of methanol is then added dropwise at room temperature. The reaction mixture is heated for about 4 hours at 45° C. The methanol is driven off in vacuo. The complex is then washed twice with either under nitrogen to remove the unreacted pyrocatechol and MeSi(OMe)₃. The solution is filtered under nitrogen. The complex is dried in vacuo at 100° C. for one day to remove the ether. This gives 12 g of complex (yield 90%). The complex, obtained in the form of a powder, must be kept under nitrogen. It is soluble in methanol and DMSO. Spectral characteristics (TMS standard): ¹³C NMR (CD₃OD) 4 signals: δ=151.6; 120.8; 113.2; 1.2 ppm. ²⁹Si NMR (CD₃OD) δ=−73.7 ppm.

EXAMPLE 2

Preparation of potassium bis(benzene-1,2-diolato)methylsilicate

By following a procedure identical to that of Example 1, the air-stable complex of the formula:

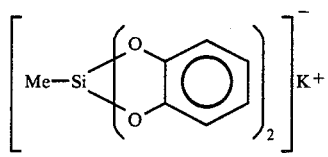

is obtained from potassium methylate.

EXAMPLE 3

Preparation of potassium bis(benzene-1,2-diolato)vinylsilicate

By following a procedure identical to that of Example 1, the air-stable complex of the formula:

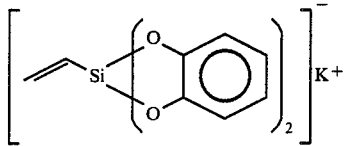

is obtained from

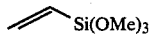

and MeOK.

EXAMPLE 4

Preparation of sodium bis(benzene-1,2-diolato)phenylsilicate

By following a procedure identical to that of Example 1, the stable complex of the formula:

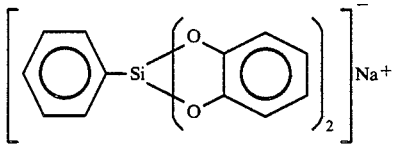

is obtained from

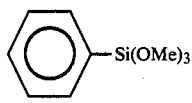

and MeONa.

EXAMPLE 5

Preparation of sodium bis(benzene-1,2-diolato)benzylsilicate

By following a procedure identical to that of Example 1, the air-stable complex of the formula:

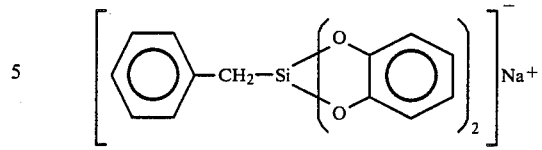

is obtained from

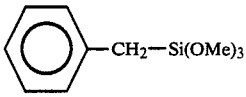

and MeONa.

EXAMPLE 6

Preparation of sodium bis(benzene-1,2-diolato)(naphth-1-yl)silicate

By following a procedure identical to that of Example 1, the stable complex of the formula:

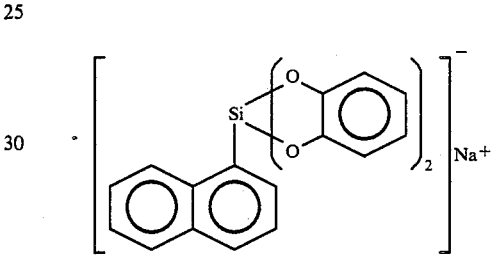

is obtained from

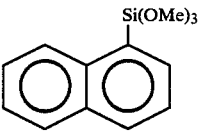

and MeONa.

EXAMPLE 7

Preparation of a mixed organosilane of the formula: R—SiR₃'

(a) General procedure

The pentacoordinate complex of the formula I (10 to 20 mmol) is suspended in anhydrous ether (50 to 100 ml) in a round-bottomed flask or a Schlenk tube. 3 equivalents of an approximately molar solution of organometallic derivative in ether are added at room temperature. The reaction mixture is heated under reflux for 1 to 2 hours. It is then hydrolyzed with 50 ml of a 25% $H_2SO_4$ solution and the silicon derivative is extracted 3 times with ether. The ether solution is washed once with 25 ml of water, twice with 25 ml of 2N sodium hydroxide solution, twice with 25 ml of water and once with a saturated solution of sodium chloride and dried over magnesium sulfate. After the solvent has been evaporated off, the silicon derivative is purified by distillation or recrystallization. It is characterized by the IR, NMR and mass spectra.

(b) Preparation of [tri(n-butyl)]methylsilane

By following the above procedure, starting from sodium bis(benzene-1,2-diolato)methylsilicate and 3 equivalents of n-butyllithium, the organosilane of the formula:

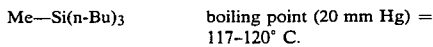
Me—Si(n-Bu)₃   boiling point (20 mm Hg) = 117–120° C.

is obtained with a yield of 43%.

(c) Preparation of methyltriphenylsilane

By following the above procedure, starting from sodium bis(benzene-1,2-diolato)methylsilicate and 3 equivalents of phenyllithium, the organosilane of the formula:

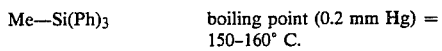
Me—Si(Ph)₃   boiling point (0.2 mm Hg) = 150–160° C.

is obtained with a yield of 63%.

(d) Preparation of triallylmethylsilane

By following the above procedure, starting from sodium bis(benzene-1,2-diolato)methylsilicate and 3 equivalents of allylmagnesium bromide, the organosilane of the formula:

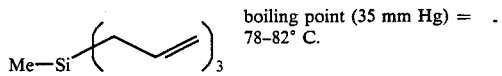
boiling point (35 mm Hg) = 78–82° C.

is obtained with a yield of 62%.

(e) Preparation of methyltri(phenylethynyl)-silane

By following the above procedure, starting from sodium bis(benzene-1,2-diolato)methylsilicate and 3 equivalents of phenylethynylmagnesium bromide, the organosilane of the formula:

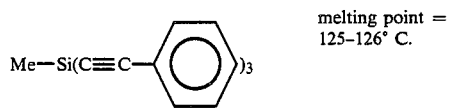
melting point = 125–126° C.

is obtained with a yield of 82%.

(f) Preparation of trimethylphenylsilane

By following the above procedure, starting from sodium bis(benzene-1,2-diolato)phenylsilicate and 3 equivalents of methyllithium, the organosilane of the formula:

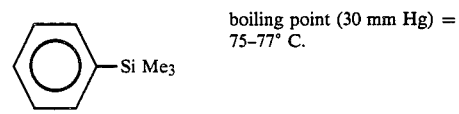
boiling point (30 mm Hg) = 75–77° C.

is obtained with a yield of 78%.

(g) Preparation of tri(n-butyl)phenylsilane

By following the above procedure, starting from sodium bis(benzene-1,2-diolato)phenylsilicate and 3 equivalents of n-butyllithium, the organosilane of the formula:

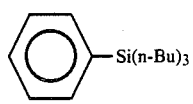
boiling point (0.05 mm Hg) = 89–92° C.

is obtained with a yield of 85%.

(h) Preparation of triallylphenylsilane

By following the above procedure, starting from sodium bis(benzene-1,2-diolato)phenylsilicate and 3 equivalents of allylmagnesium bromide, the organosilane of the formula:

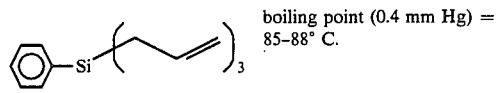
boiling point (0.4 mm Hg) = 85–88° C.

is obtained with a yield of 53%.

(i) Preparation of [tri(hex-1-ynyl)]phenylsilane

By following the above procedure, starting from sodium bis(benzene-1,2-diolato)phenylsilicate and 3 equivalents of (hex-1-ynyl)magnesium bromide, the organosilane of the formula:

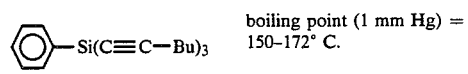
boiling point (1 mm Hg) = 150–172° C.

is obtained with a yield of 54%.

EXAMPLE 8

Preparation of a monohydrogenoorganosilane of the formula: RSiR₂'H

(a) General procedure

The pentacoordinate complex of the formula I (10 to 20 mmol) is suspended in anhydrous ether (50 to 100 ml) in a round-bottomed flask or a Schlenk tube. 2 equivalents of an approximately molar solution of organometallic derivative in ether are added at room temperature. The reaction mixture is heated under reflux for 1 to 2 hours and then poured into an excess (n g) of LiAlH₄ suspended in ether, after which the reaction mixture is stirred at room temperature for 3 hours. It is subsequently hydrolyzed with n ml of water, followed by n ml of 15% sodium hydroxide solution and then 3.n ml of water. The precipitate formed is filtered off and washed with ether. The filtrates are washed once with water and dried over magnesium sulfate.

After the solvent has been evaporated off, the silicon derivative is purified by distillation or recrystallization. It is characterized by the IR, NMR and mass spectra.

(b) Preparation of dibenzylmethylsilane

By following the above procedure, starting from sodium bis(benzene-1,2-diolato)methylsilicate and 2 equivalents of benzylmagnesium bromide, the organosilane of the formula:

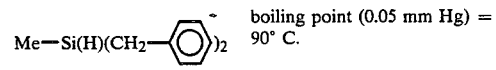
boiling point (0.05 mm Hg) = 90° C.

is obtained with a yield of 86%.

(c) Preparation of methyldiphenylsilane

By following the above procedure, starting from sodium bis(benzene-1,2-diolato)methylsilicate and 2 equivalents of phenyllithium, the organosilane of the formula:

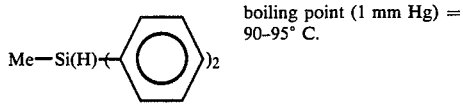

boiling point (1 mm Hg) = 90–95° C.

is obtained with a yield of 60%.

(d) Preparation of 1-methyl-2,5-diphenylsilacyclopentadiene

By following the above procedure, starting from sodium bis(benzene-1,2-diolato)methylsilicate and only one equivalent of

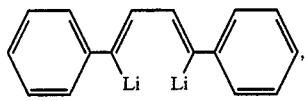

the organosilane of the formula:

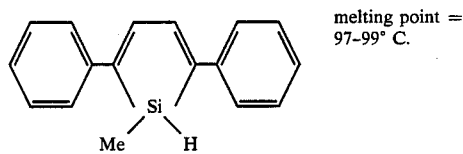

melting point = 97–99° C.

is obtained with a yield of 51%.

(e) Preparation of dimethylphenylsilane

By following the above procedure, starting from sodium bis(benzene-1,2-diolato)phenylsilicate and 2 equivalents of methyllithium, the organosilane of the formula:

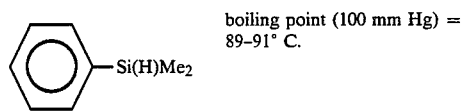

boiling point (100 mm Hg) = 89–91° C.

is obtained with a yield of 40%.

(f) Preparation of dimethylphenylsilane

By following the above procedure, starting from sodium bis(benzene-1,2-diolato)phenylsilicate and 2 equivalents of methylmagnesium bromide, the organosilane of the formula:

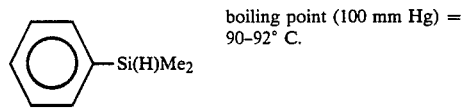

boiling point (100 mm Hg) = 90–92° C.

is obtained with a yield of 65%.

(g) Preparation of diethylphenylsilane

By following the above procedure, starting from sodium bis(benzene-1,2-diolato)phenylsilicate and 2 equivalents of ethylmagnesium bromide, the organosilane of the formula:

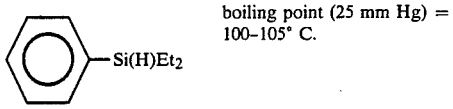

boiling point (25 mm Hg) = 100–105° C.

is obtained with a yield of 40%.

(h) Preparation of di(n-butyl)phenylsilane

By following the above procedure, starting from sodium bis(benzene-1,2-diolato)phenylsilicate and 2 equivalents of n-butyllithium, the organosilane of the formula:

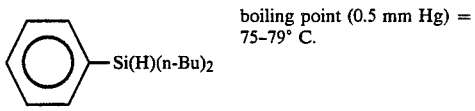

boiling point (0.5 mm Hg) = 75–79° C.

is obtained with a yield of 57%.

(i) Preparation of di(isopropyl)phenylsilane

By following the above procedure, starting from sodium bis(benzene-1,2-diolato)phenylsilicate and 2 equivalents of isopropylmagnesium bromide, the organosilane of the formula:

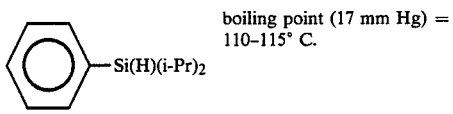

boiling point (17 mm Hg) = 110–115° C.

is obtained with a yield of 45%.

(j) Preparation of 1,2,5-triphenylsilacyclopentadiene

By following the above procedure, starting from sodium bis(benzene-1,2-diolato)phenylsilicate and only one equivalent of

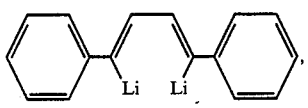

the organosilane of the formula:

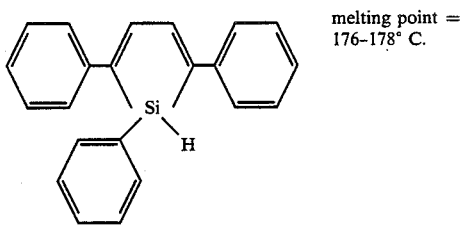

melting point = 176–178° C.

is obtained with a yield of 40%.

EXAMPLE 9

Preparation of dihydrogenosilanes 20 mmol of sodium bis(benzene-1,2-diolato)phenylsilicate and 0.251 g of bis(cyclopentadienyl)titanium dichloride (1 mmol) are suspended in 60 ml of anhydrous ether under an argon atmosphere. 1 equivalent of a solution of tert.-butylmagnesium bromide in ether is added dropwise at room temperature. The reaction mixture is then heated under reflux for about 5 hours. It is hydrolyzed with 4N HCl. The aqueous phase is extracted 3 times with ether. The organic phase is washed with sodium hydroxide solution, followed by water until the washings are neutral, and then dried over MgSO$_4$. On distillation, this gives the dihydrogenosilane of the formula:

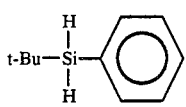

boiling point (23 mm Hg) = 80–85° C.

with a yield of 50%. Subsequent reaction with a different organometallic derivative, for example methylmagnesium bromide, gives a monohydrogenosilane of the formula:

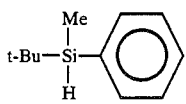

Hydroxylation of this type of monohydrogeno derivative leads to the formation of silanols of the general formula:

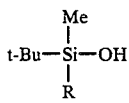

which are useful as drugs or as intermediates for the synthesis of drugs.

What is claimed is:

1. A pentacoordinate silicon complex which corresponds to the general formula I:

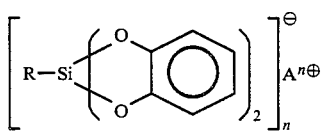

in which:
R denotes an alkyl, alkenyl, alkynyl, aryl, aralkyl, aralkenyl, aralkynyl or alkylaryl radical in which the aliphatic fragments are linear, branched or cyclic and contain from 1 to 20 carbon atoms,
A represents an alkali metal or alkaline earth metal, with the proviso however that A represents neither sodium nor potassium when R is a phenyl radical, and
n=1 or 2.

2. A process for the preparation of complexes of the general formula I as claimed in claim 1, which comprises reacting a silicon derivative of the general formula II:

R—SiY (II)

in which:
R has the meaning given in claim 1 and
Y represents a C$_1$ to C$_6$ trialkoxy, trihalogeno, C$_1$ to C$_6$ dialkoxyhydrogeno or dihalogenohydrogeno group, with pyrocatechol in the presence of a base.

3. The process as claimed in claim 2, wherein the said base is an alkali metal alcoholate or alkaline earth metal alcoholate, in particular prepared in situ in the reaction medium.

4. The process as claimed in one of claims 2 and 3, wherein the reaction is carried out in an anhydrous solvent medium, especially in an alcoholic medium, and under an inert atmosphere.

5. An application of the complexes of the general formula I:

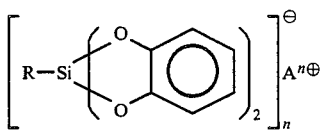

in which:
R denotes an alkyl, alkenyl, alkynyl, aryl, aralkyl, aralkenyl, aralkynyl or alkylaryl radical in which the aliphatic fragments are linear, branched or cyclic and contain from 1 to 20 carbon atoms,
A represents an alkali metal or alkaline earth metal and
n=1 or 2,
to the preparation of organosilanes of the formula III:

RR'R"SiR''' (III)

in which:
R has the meaning given above,
R' denotes a radical R and
R" and R''' denote a hydrogen atom or a radical R, it also being possible for R' and R" to form a ring with the silicon atom,
which comprises reacting an organometallic derivative with the abovementioned complex of the general formula I.

6. The application as claimed in claim 5, wherein the organometallic derivative is an alkali metal organometallic derivative of the general formula IV:

R—Alk (IV)

in which:
R has the meaning given in claim 1 and
Alk denotes an alkali metal.

7. The application as claimed in claim 5, wherein the organometallic derivative is an organomagnesium halide of the general formula V:

R—Mg—X (V)

in which:
R has the meaning given in claim 1 and
X denotes a halogen atom.

8. The application as claimed in claim 5, wherein the organometallic derivative is an organozinc derivative of the general formula VI:

R$_2$Zn (VI)

in which:
R has the meaning given in claim 1.

9. The application as claimed in claim 5, wherein the organometallic derivative is an organodimagnesium derivative of the general formula VII:

(VII)

in which:

Z denotes an alkylene or alkylene radical containing 3 to 5 carbon atoms and

X denotes a halogen atom.

10. The application as claimed in claim 5, wherein the organometallic derivative is a di(alkali metal)organometallic derivative of the general formula VIII:

(VIII)

in which:

Z denotes an optionally substituted alkylene or alkenylene radical containing 3 to 5 carbon atoms and Alk denotes an alkali metal.

11. The application as claimed in one of claims 5 to 10, wherein the reaction is carried out by heating under reflux in an anhydrous solvent medium and under an inert atmosphere.

12. The application as claimed in one of claims 5 to 11, wherein a reducing agent, in particular an inorganic hydride such as lithium aluminum hydride, is added to the medium, after the organometallic derivative has reacted, to give a monohydroorganosilane of the formula III in which R''' represents a hydrogen atom.

13. The application as claimed in one of claims 5 to 11, wherein the reaction is carried out with an organometallic derivative in the presence of bis(cyclopentadienyl)titanium dichloride to give a hydrogenoorganosilane.

* * * * *